United States Patent
Nash et al.

(10) Patent No.: US 6,796,309 B2
(45) Date of Patent: Sep. 28, 2004

(54) TRACHEAL TUBES

(75) Inventors: John Edward Nash, Hythe (GB); Paul Benjamin Ridout, Edmondsham (GB)

(73) Assignee: Smith Group PLC, London (GB)

(*) Notice: Subject to any disclaimer, the term of this patent is extended or adjusted under 35 U.S.C. 154(b) by 0 days.

(21) Appl. No.: 10/005,227

(22) Filed: Dec. 7, 2001

(65) Prior Publication Data

US 2002/0078962 A1 Jun. 27, 2002

(30) Foreign Application Priority Data

Dec. 23, 2000 (GB) .............................................. 0031598
Mar. 1, 2001 (GB) .............................................. 0105037

(51) Int. Cl.⁷ ........................................................ A61M 16/00
(52) U.S. Cl. ............................. 128/207.14; 128/207.15
(58) Field of Search ....................... 128/207.14, 207.15, 128/200.24, 200.26, 207.16, 207.18; 604/93.01, 96.01, 98.01, 102.01, 118, 119, 128

(56) References Cited

U.S. PATENT DOCUMENTS

| | | | | |
|---|---|---|---|---|
| 2,854,982 A | * | 10/1958 | Pagano | 128/207.15 |
| 3,593,713 A | * | 7/1971 | Bogoff | 128/207.15 |
| 4,156,428 A | * | 5/1979 | Henkin | 128/207.15 |
| 4,305,392 A | * | 12/1981 | Chester | 128/207.15 |
| 4,327,721 A | | 5/1982 | Goldin et al. | |
| 4,607,635 A | * | 8/1986 | Heyden | 128/207.15 |
| 4,674,495 A | * | 6/1987 | Orr | 128/207.14 |
| 4,762,125 A | * | 8/1988 | Leiman et al. | 128/207.15 |
| 4,840,173 A | | 6/1989 | Porter, III | |
| 4,955,375 A | * | 9/1990 | Martinez | 128/207.15 |
| 5,067,497 A | * | 11/1991 | Greear et al. | 128/207.15 |
| 5,143,062 A | * | 9/1992 | Peckham | 128/207.14 |
| 5,201,310 A | * | 4/1993 | Turnbull | 128/207.15 |
| 5,311,864 A | * | 5/1994 | Huerta | 128/207.15 |
| 5,372,131 A | * | 12/1994 | Heinen, Jr. | 128/207.15 |
| 5,501,215 A | * | 3/1996 | Huerta | 128/207.15 |
| 5,582,167 A | * | 12/1996 | Joseph | 128/207.15 |
| 5,819,723 A | * | 10/1998 | Joseph | 128/207.14 |
| 5,832,920 A | * | 11/1998 | Field | 128/207.14 |
| 6,062,223 A | * | 5/2000 | Palazzo et al. | 128/207.15 |
| 6,254,591 B1 | * | 7/2001 | Roberson | 604/541 |
| 6,460,540 B1 | * | 10/2002 | Klepper | 128/207.14 |
| 6,725,862 B2 | * | 4/2004 | Klinberg et al. | 128/207.14 |

FOREIGN PATENT DOCUMENTS

| | | | | |
|---|---|---|---|---|
| JP | 0005340 | | 1/1998 | |
| JP | 10-5340 | * | 1/1998 | 128/207.15 |
| JP | 10005340 | | 1/1998 | |
| JP | 1998-124102 | | 5/1998 | |
| JP | 1998-124103 | | 5/1998 | |
| JP | 10-337326 | * | 12/1998 | 128/207.15 |
| WO | WO 99/38548 | | 8/1995 | |

OTHER PUBLICATIONS

Stuttmann R. et al., "What is the benefit of subglottic suction?!", Der Anaesthesist, Germany, Feb. 1987, vol. 36, No. 2, pp 87–90.

* cited by examiner

Primary Examiner—Henry Bennett
Assistant Examiner—Teena Mitchell
(74) Attorney, Agent, or Firm—Louis Woo

(57) ABSTRACT

A tracheostomy tube has a sealing cuff inflated by an inflation tube extending in a channel along one side of the tracheostomy tube. A suction tube extends in a channel along the opposite side of the tracheostomy tube. The suction tube extends to the upper end of the sealing cuff and opens into a recess on the outside of the tracheostomy tube through a side opening oriented at right angles to the radius of the tracheostomy tube. The recess extends around about 90° of the tube towards its outer curve so that secretions collecting in this region can be removed.

8 Claims, 5 Drawing Sheets

TRACHEAL TUBES

BACKGROUND OF THE INVENTION

This invention relates to tracheal tubes.

Cuffed tracheal tubes, in particular, tracheostomy tubes, can present a problem in that secretions produced in the trachea may collect outside the tube above the cuff, providing a site for the accumulation of bacteria and infection.

Various proposals have been made previously for removing such secretions by suctioning from above the cuff. U.S. Pat. No. 4,607,635 describes a tracheal tube having a channel open at various locations along its length and through which a suction catheter can be inserted to remove secretions at any desired location above the cuff. In U.S. Pat. No. 4,305,392 there is described a tracheal tube with a bulbous chamber above the cuff in which secretions are collected for removal through a suction lumen extending through the wall of the tube. U.S. Pat. No. 4,840,173 describes a catheter having a suction tube projecting over the proximal collar of the cuff to increase the amount of secretions that can be collected. GB 2250440 describes a tube where the upper end of the cuff is everted within the cuff so that it does not provide any obstruction to locating a suction opening as close as possible to the cuff.

One difficulty with previous tubes is in ensuring that the maximum amount of secretions are removed. A further problem with some previous tubes is that when suction is applied, this can suck adjacent tissue onto the suction opening, thereby closing it or valving off the suction path.

BRIEF SUMMARY OF THE INVENTION

It is an object of the present invention to provide an alternative tracheal tube.

According to the present invention there is provided a tracheal tube having a sealing cuff towards one end and a suction lumen extending longitudinally along a part of the length of the tube and having an opening just above the upper end of the cuff on the outside of the tube, the opening of the suction lumen opening into a recess on the outside of the tube, and the recess extending laterally away from the opening such that secretions collecting at a location laterally displaced from the opening can be removed via the recess and the suction lumen.

The tracheal tube is preferably curved along a part at least of its length, the suction lumen extending along one side of the tube and the recess extending from the opening to a location closer to the outside curve of the tube. The recess preferably extends through substantially 90° around the circumference of the tracheal tube. The suction tube may be provided by a separate tube attached to the outside of the tracheal tube, preferably the suction tube extends along a channel formed in the outside of the tracheal tube. The suction tube may open into the recess through a side opening in the suction tube and preferably the side opening is oriented at substantially right angles to the radius of the tracheal tube. The tracheal tube preferably includes an inflation lumen opening into the cuff and the inflation lumen may extend along the tracheal tube diametrically opposite the suction lumen.

A tracheostomy tube according to the present invention will now be described, by way of example, with reference to the accompanying drawings.

DETAILED DESCRIPTION

Figure 1:
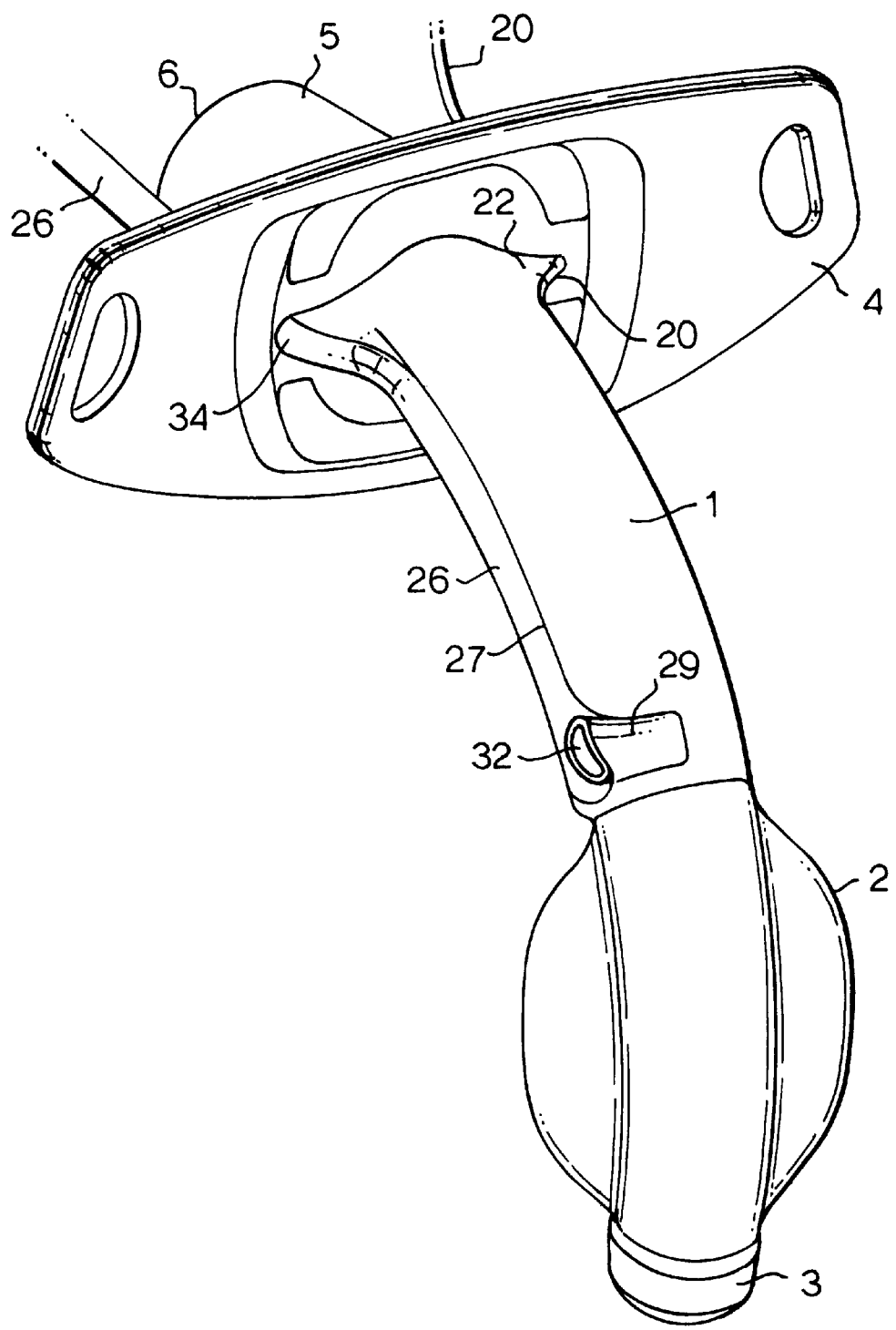
FIG. 1 is a perspective view of the tube.
Figure 2:
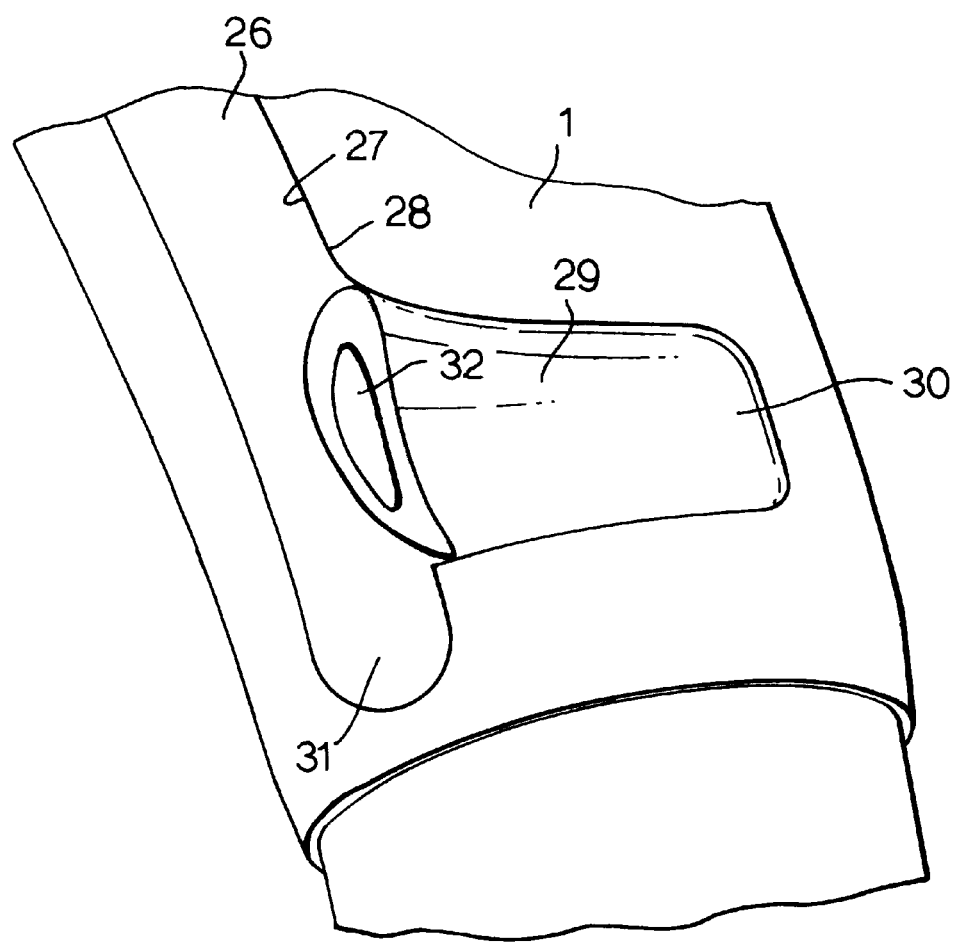
FIG. 2 is an enlarged perspective view of a part of the tube, with the cuff omitted, for clarity.
Figure 3:
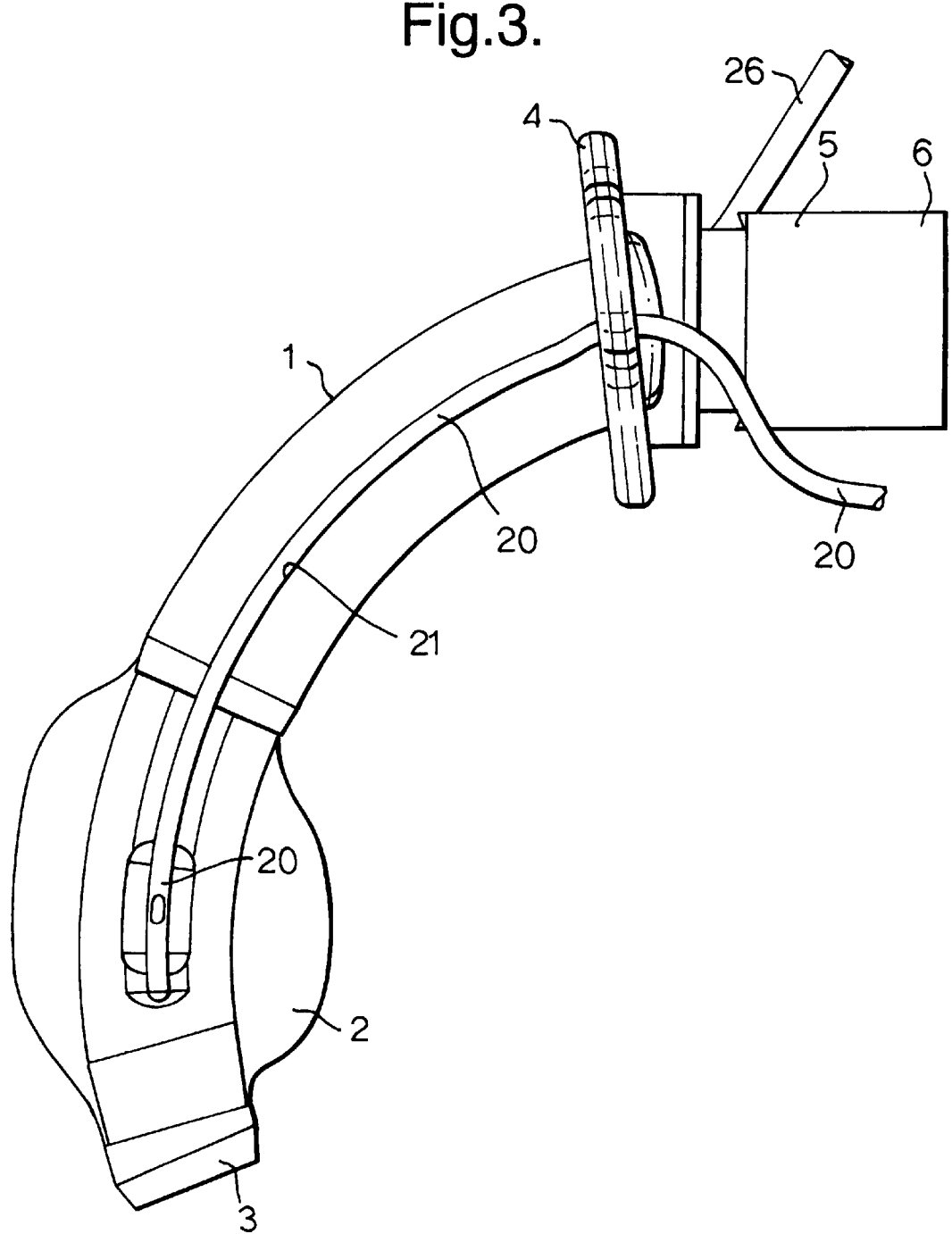
FIG. 3 is a side elevation view of the tube from one side.
Figure 4:
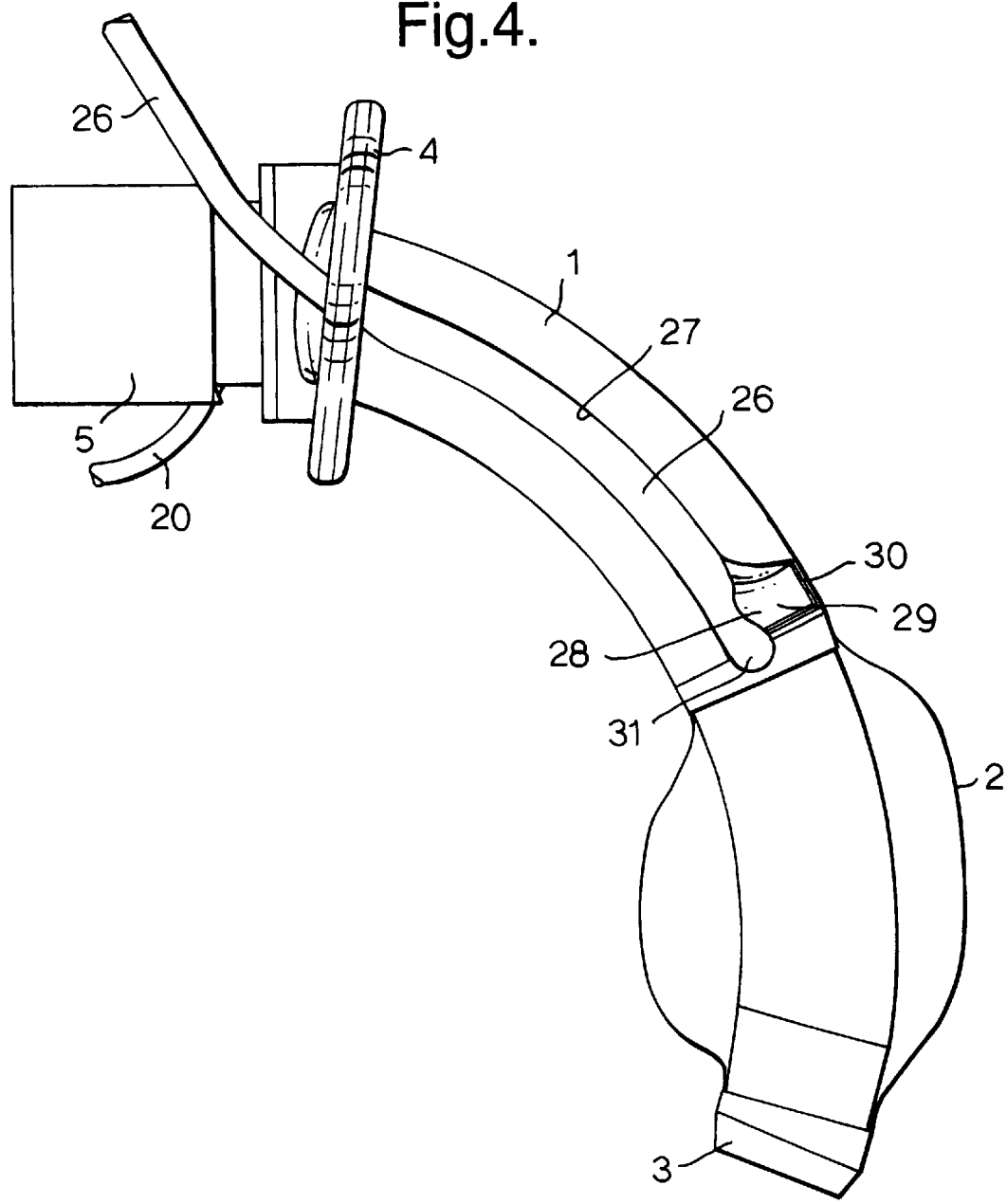
FIG. 4 is a side elevation view of the tube from the opposite side.
Figure 5:
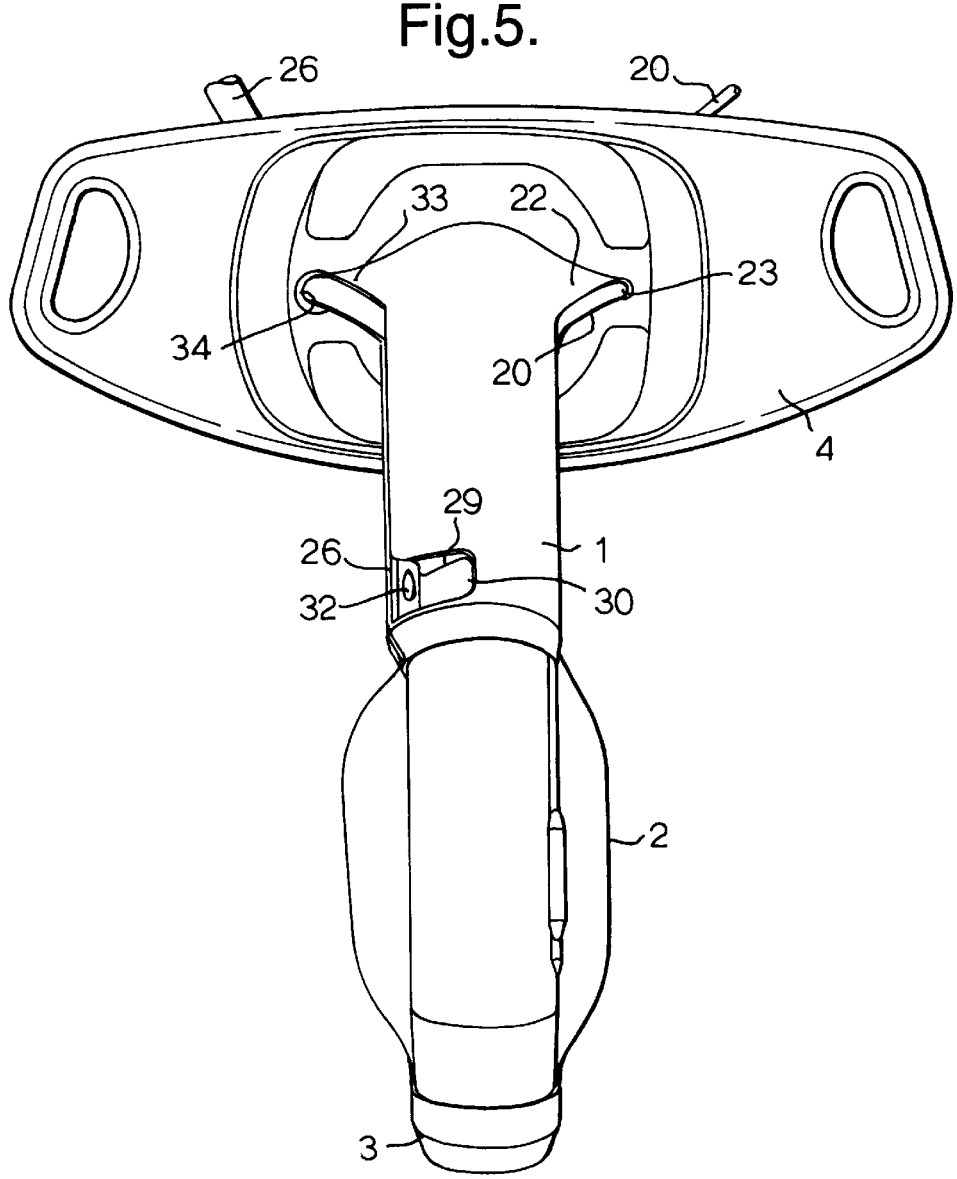
FIG. 5 is a front elevation view of the tube.

With reference first to FIGS. 1 to 5, the tube includes a tubular shaft 1 curved along its length and having an inflatable sealing cuff 2 towards its patient end 3. The tube also has a flange 4 and coupling 5 at its rear or machine end 6. The shaft 1, flange 4 and coupling 5 are integrally moulded with one another as a single piece from a plastics material, such as PVC.

The cuff 2 is inflated by means of an inflation lumen provided by a small-bore tube 20 extending along one side of the shaft 1 in a semi-cylindrical channel 21 moulded into its outside surface. The machine end of the channel 21 leads to an outwardly-inclined ramp 22 on the shaft 1, which supports the inflation tube 20 where it extends through a hole 23 in the flange 4. The machine end of the inflation tube 20 is terminated by a conventional connector and inflation indicator (not shown).

On its opposite side, the tube has a suction tube 26 extending parallel to the inflation tube 20. The suction tube 26 has a larger diameter than the inflation tube 20 and extends in a similar semi-cylindrical channel 27 moulded longitudinally along the outside surface of the shaft 1. The forward or patient end 28 of the channel 27 opens into a recess or gutter 29 in the outer surface of the shaft 1. The gutter 29 extends laterally at right-angles to the channel 27 through about 90° around the circumference of the shaft 1, so that its far end 30 is located on the outside of the curve of the shaft. The patient end 31 of the suction tube 26 is closed, the tube opening just rearwardly of its patient end through an elongate side opening 32. The side opening 32 is oriented at right angles to the radius of the shaft 1 to face into the gutter 29. This arrangement presents less risk of occlusion because the opening 32 does not face outwardly towards the patient tissue; the relatively large area of the gutter 29 means that it is less likely to be completely obstructed by contact with adjacent tissue.

The machine end of the channel 27 leads to an outwardly-inclined ramp 33 on the shaft 1, which supports the suction tube 26 where it extends through a hole 34 in the flange 4 diametrically opposite the inflation tube hole 23.

The gutter 29 enables suctioning of the region on the outside of the curve of the tube, which lies posteriorly of the trachea in use, where most secretions collect when the patient is in the usual supine position. This helps ensure that the maximum amount of secretions are removed when suction is applied to the machine end of the suction tube 26. The suction tube 26 still, however, extends along the side of the tube, which is the preferred location anatomically because it minimizes the risk of trauma to tracheal cartilages. This enables the diameter of the suction tube to be a maximum, so as to reduce the risk of blockages.

Figure 6:
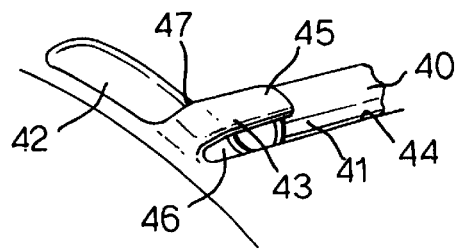
FIG. 6 is a perspective view of a part of a modified tube.

The suction tube need not open through a side opening. The tracheal tube could have a suction tube 40 that opens at its end 41 in the manner shown in FIG. 6. In this arrangement, the suction tube 40 terminates at the upper end of the gutter 42 and the tracheal tube is moulded with an integral, outwardly-projecting elongate limb 43 located at the patient side of the gutter in line with the channel 44. The limb 43 is bent down and its free end 45 is bonded to the outside of the suction tube 40 close to its end. In this way, the limb 43 forms a longitudinally-extending bridge with the suction tube 40 and is spaced above the surface of the shaft of the tracheal tube so that the suction tube opens on opposite sides of the limb through apertures 46 and 47. The limb 43 forms an anti-occlusion formation for the suction tube 40 and, because it extends longitudinally and covers the end 41 of the tube, it smoothes contact with tissue during insertion, thereby further reducing trauma.

It will be appreciated that the invention is not confined to tracheostomy tubes but could be used in other tracheal tubes.

What we claim is:

1. A tracheal tube comprising: a tubular shaft curved along a part at least of its length; a sealing cuff towards one end of the shaft; a single suction lumen extending longitudinally along one side of said shaft along a part of the length of the shaft, said suction lumen having an opening just above an upper end of said cuff on an outside of said shaft; and a recess in the outer surface of said shaft, said opening being located to one side of said recess and said recess extending laterally away from said opening to a location adjacent an outside curve of said shaft such that secretions collecting at the outside curve of said shaft can be removed via said recess and said suction lumen.

2. A tracheal tube according to claim 1, wherein said recess extends through substantially 90° around the circumference of said shaft.

3. A tracheal tube according to claim 1, wherein said suction lumen is provided by a separate suction tube attached to an outside of said shaft.

4. A tracheal tube according to claim 3, wherein said shaft has a channel formed on its outside, and wherein said suction tube extends along said channel.

5. A tracheal tube according to claim 3, wherein said suction tube has a side opening, and wherein said suction tube opens into said recess through said side opening.

6. A tracheal tube according to claim 5, wherein said side opening is oriented at substantially right angles to a radius of said shaft.

7. A tracheal tube according to claim 1 including an inflation lumen opening into said cuff, wherein said inflation lumen extends along said shaft diametrically opposite said suction lumen.

8. A tracheal tube comprising: a tubular shaft curved along a part at least of its length; a sealing cuff towards one end of said shaft; a single suction tube extending longitudinally along one side of said shaft, said suction tube being closed at its end and having a side opening just above an upper end of said cuff in the outer surface of said shaft; and a recess on the outside of said shaft, said tube being located at one end of said recess and said recess extending laterally away from said opening to a location adjacent an outside curve of said shaft, wherein said side opening of said suction tube is oriented at substantially right angles to a radius of said shaft and opens into said recess such that secretions collecting at the outside curve of said shaft can be removed via said recess and said side opening of said suction tube.

* * * * *